United States Patent
Ono et al.

(10) Patent No.: US 8,697,125 B2
(45) Date of Patent: Apr. 15, 2014

(54) TABLET PREPARATION WITHOUT CAUSING A TABLETING TROUBLE

(75) Inventors: Akihiko Ono, Osaka (JP); Shigeyuki Marunaka, Osaka (JP); Makoto Fukuta, Osaka (JP)

(73) Assignee: Takeda Pharmaceutical Company Limited, Osaka (JP)

(*) Notice: Subject to any disclaimer, the term of this patent is extended or adjusted under 35 U.S.C. 154(b) by 358 days.

(21) Appl. No.: 12/449,256

(22) PCT Filed: Jan. 30, 2008

(86) PCT No.: PCT/JP2008/051896
§ 371 (c)(1),
(2), (4) Date: Jul. 30, 2009

(87) PCT Pub. No.: WO2008/093878
PCT Pub. Date: Aug. 7, 2008

(65) Prior Publication Data
US 2009/0318482 A1     Dec. 24, 2009

(30) Foreign Application Priority Data
Feb. 1, 2007 (JP) ................. 2007-023584

(51) Int. Cl.
*A61K 9/20* (2006.01)
*A61K 31/717* (2006.01)
*A61K 31/047* (2006.01)
*A61K 31/505* (2006.01)
*A61K 31/7004* (2006.01)

(52) U.S. Cl.
USPC ............ 424/465; 424/464; 424/488; 514/57; 514/274; 514/738

(58) Field of Classification Search
USPC ........................................ 424/464
See application file for complete search history.

(56) References Cited

U.S. PATENT DOCUMENTS

| | | | |
|---|---|---|---|
| 5,462,747 A | 10/1995 | Radebaugh et al. | |
| 6,039,974 A | 3/2000 | MacLaren et al. | |
| 2002/0136775 A1* | 9/2002 | Thosar et al. | 424/499 |
| 2004/0214804 A1* | 10/2004 | Gulve et al. | 514/171 |
| 2005/0106244 A1 | 5/2005 | Kushla et al. | |
| 2005/0232991 A1 | 10/2005 | Hanshew, Jr. et al. | |
| 2005/0261271 A1 | 11/2005 | Feng et al. | |
| 2007/0060528 A1 | 3/2007 | Christopher et al. | |
| 2007/0066635 A1 | 3/2007 | Andres et al. | |
| 2009/0105265 A1* | 4/2009 | Kamali et al. | 514/249 |

FOREIGN PATENT DOCUMENTS

| | | |
|---|---|---|
| DE | 20-2006-000591 U1 | 3/2006 |
| JP | 09-143065 A | 6/1997 |
| JP | 10-059842 A | 3/1998 |
| JP | 2002-179559 A | 6/2002 |
| JP | 2004-189653 A | 7/2004 |
| WO | WO 97/44022 A1 | 11/1997 |
| WO | WO 99/09959 | 3/1999 |
| WO | WO 00/33847 | 6/2000 |
| WO | WO 01/41762 A2 | 6/2001 |
| WO | WO 02/03987 A2 | 1/2002 |
| WO | WO 2005/067976 A1 * | 7/2005 |
| WO | WO 2007/026261 A2 | 3/2007 |
| WO | WO 2007/033266 A3 | 3/2007 |

OTHER PUBLICATIONS

International Search Report mailed Mar. 27, 2008 in prior PCT/JP2008/051896, 8 pages.

* cited by examiner

*Primary Examiner* — Ernst Arnold
(74) *Attorney, Agent, or Firm* — Foley & Lardner LLP

(57) ABSTRACT

The present invention provides a tablet without causing a tableting trouble, which is superior in the tablet formability, dissolution property of pharmaceutically active ingredient, and the like.

9 Claims, No Drawings

TABLET PREPARATION WITHOUT CAUSING A TABLETING TROUBLE

CROSS-REFERENCE TO RELATED APPLICATIONS

This application is a National Stage application of PCT/JP2008/051896, filed Jan. 30, 2008, which claims priority from Japanese application JP 2007-023584, filed Feb. 1, 2007.

TECHNICAL FIELD

The present invention relates to a solid preparation (specifically tablet) containing a pharmaceutically active ingredient easily inducing a tableting trouble.

BACKGROUND OF THE INVENTION

Depending on the properties of the compound used as a pharmaceutically active ingredient, a tableting trouble often occurs in a tableting (punching) step during production of tablets.

To avoid a tableting trouble, methods such as increasing the amount of magnesium stearate used as a lubricant, elongating the mixing time and the like can be employed. When the amount of magnesium stearate in a tablet is increased, the tableting trouble can be reduced. However, problems in the quality such as degraded formability (e.g., low tablet hardness and the like), delayed dissolution of pharmaceutically active ingredients, and the like easily occur. In addition, an elongated mixing time impairs producibility of the tablet.

As other methods for avoiding tableting trouble, a method including punching a pharmaceutically active ingredient easily inducing a tableting trouble, in the presence of a crystalline powder having an average particle size of 1-100 μm has been reported (JP-A-10-59842).

DISCLOSURE OF THE INVENTION

There is a demand for provision of a tablet superior in the tablet formability, dissolution property of a pharmaceutically active ingredient and the like, without causing a tableting trouble during tableting of a pharmaceutically active ingredient easily inducing a tableting trouble.

The present inventors have conducted intensive studies in an attempt to solve the above-mentioned problems and found that degradation of tablet formability such as decreased tablet hardness, delayed dissolution of a pharmaceutically active ingredient and the like can be prevented without causing a tableting trouble when tableting a pharmaceutically active ingredient, which easily induces a tableting trouble, by individually preparing (A) a granule containing the pharmaceutically active ingredient and microcrystalline cellulose (also referred to as component (A) in the present specification), and (B) a tableting aid containing magnesium stearate and microcrystalline cellulose (also referred to as component (B) in the present specification) rather than mixing the starting materials at once, mixing them and punching the mixture, and further studies resulted in the completion of the present invention.

Accordingly, the present invention relates to
[1] a tablet comprising the following (A) and (B):
(A) a granule comprising a pharmaceutically active ingredient easily inducing a tableting trouble and microcrystalline cellulose;
(B) a tableting aid comprising magnesium stearate and microcrystalline cellulose
(the tablet of the above-mentioned [1] is sometimes to be referred to as "the tablet of the present invention" in the present specification),
[2] a tablet comprising the following (A) and (B):
(A) a granule comprising compound A (to be mentioned later) or a salt thereof as a pharmaceutically active ingredient and microcrystalline cellulose;
(B) a tableting aid comprising magnesium stearate and microcrystalline cellulose
(the tablet of the above-mentioned [2] is also encompassed in "the tablet of the present invention" in the present specification),
[3] the tablet of the above-mentioned [1] or [2], wherein the content of the microcrystalline cellulose of the aforementioned (A) and the microcrystalline cellulose of the aforementioned (B) in the tablet is 5-40 wt % and 2-20 wt %, respectively,
[4] the tablet of the above-mentioned [1] or [2], wherein the hardness is 70-200 N,
[5] the tablet of the above-mentioned [1] or [2], wherein not less than 85% of the pharmaceutically active ingredient is dissolved out in 15 min when the tablet is subjected to a dissolution test according to the Paddle Method at 37° C., 50 rpm using 0.01N hydrochloric acid or the Japanese Pharmacopoeia 2nd fluid (pH 6.8) as a test solution,
[6] the tablet of the above-mentioned [1] or [2], wherein the granule of the aforementioned (A) further comprises mannitol,
[7] a method of producing a tablet, which comprises mixing (A) a granule comprising a pharmaceutically active ingredient easily inducing a tableting trouble and microcrystalline cellulose, and (B) a tableting aid comprising magnesium stearate and microcrystalline cellulose, and then punching the mixture,
[8] a method of producing a tablet, which comprises mixing (A) a granule comprising compound A or a salt thereof as a pharmaceutically active ingredient and microcrystalline cellulose, and (B) a tableting aid comprising magnesium stearate and microcrystalline cellulose, and then punching the mixture,
[9] the method of the above-mentioned [7] or [8], wherein the content of the microcrystalline cellulose of the aforementioned (A) and the microcrystalline cellulose of the aforementioned (B) in the tablet is 5-40 wt % and 2-20 wt %, respectively,
[10] the method of the above-mentioned [7] or [8], wherein the granule of the aforementioned (A) further comprises mannitol,
[11] a tablet obtained by the method of the above-mentioned [7] or [8];
and the like.

According to the present invention, a tablet containing a pharmaceutically active ingredient easily inducing a tableting trouble, which is superior in the tablet formability, dissolution property of the pharmaceutically active ingredient, and the like can be provided without causing a tableting trouble when tableting.

DETAILED DESCRIPTION OF THE INVENTION

The component (A) in the tablet of the present invention is a granule containing a pharmaceutically active ingredient easily inducing a tableting trouble and microcrystalline cellulose (hereinafter sometimes to be abbreviated as "the granule of the present invention").

In the present specification, the "granule" means a particle having an almost uniform shape and size, which is obtained by granulating a starting material such as powder, bulk, solution, molten liquid and the like by a wet granulation method, a dry granulation method or a heating granulation method.

The average particle size of the granule of the present invention is generally not less than 1000 μm for not more than 20%, not more than 150 μm for not more than 65% (with 16 M sieve, on (remaining on the sieve): not more than 20%; with 100 M sieve, pass (passed through sieve): not more than 65%), preferably not less than 1000 μm for not more than 10%, not more than 150 μm for not more than 55% (with 16 M sieve, on: not more than 10%; with 100 M sieve, pass: not more than 55%). Here, the average particle size is, for example, a value obtained by measuring the weight of the granule remaining on the sieve when sieved with a standard sieve.

The shape and size of the granule may change during the preparation making process (e.g., tableting step) for producing the tablet of the present invention.

In the present specification, the "tableting trouble" means unpreferable phenomena that occur during tableting, for example, sticking (phenomenon of attachment of powder to punch), binding (phenomenon of increased friction between die and tablet), capping (phenomenon of cap-like detachment of tablet), laminating (phenomenon of layer-like detachment of tablet) and the like.

The pharmaceutically active ingredient easily inducing a tableting trouble in the present invention (sometimes abbreviated as a "pharmaceutically active ingredient" in the present specification) refers to a pharmaceutically active ingredient that easily shows the above-mentioned phenomena during tableting.

Specific examples of the pharmaceutically active ingredient easily inducing a tableting trouble include the compound described in US-A-2005/0261271, preferably 2-[[6-[(3R)-3-amino-1-piperidinyl]-3,4-dihydro-3-methyl-2,4-dioxo-1(2H)-pyrimidinyl]methyl]-benzonitrile (general name: Alogliptin; sometimes to be abbreviated as "compound A" in the present specification), or a salt thereof; ibuprofen; vitamin C; trimebutine maleate; and the like.

Examples of the salt of compound A include a pharmacologically acceptable salt, such as a salt with inorganic acid, a salt with organic acid, a salt with basic or acidic amino acid and the like.

Preferable examples of the salt with inorganic acid include salts with hydrochloric acid, hydrobromic acid, nitric acid, sulfuric acid, phosphoric acid and the like.

Preferable examples of the salt with organic acid include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like, and preferable examples of the salt with acidic amino acid include salts with aspartic acid, glutamic acid and the like.

Preferable examples of the salt of compound A include salts with benzoic acid, trifluoroacetic acid, p-toluenesulfonic acid, hydrochloric-acid and the like, more preferably a salt with benzoic acid.

The compound A may be a solvate (e.g., hydrate etc.) or a non-solvate.

The compound A may be labeled with an isotope (e.g., $^3H$, $^{14}C$, $^{35}S$, $^{125}I$) and the like.

Furthermore, deuterium-converted compound wherein $^1H$ has been converted to $^2H(D)$ are also encompassed in the compound A.

In the granule of the present invention, the "pharmaceutically active ingredient easily inducing a tableting trouble" is used in an amount corresponding to the content of generally 1-75 wt %, preferably 1-50 wt %, of one tablet of the present invention.

Particularly, when compound A or a salt thereof is used as a pharmaceutically active ingredient, it is used in an amount corresponding to the content of preferably 1-50 wt %, more preferably 1-35 wt %, as compound A (free form) in one tablet of the present invention.

While microcrystalline cellulose to be used in the present invention is not particularly limited as long as it can be used as an additive for pharmaceutical products, and microcrystalline cellulose, microcrystalline cellulose (particles), microcrystalline cellulose (fine particles) and the like may be used singly or two or more kinds thereof may be used in a mixture.

In the granule of the present invention, microcrystalline cellulose is used in an amount corresponding to the content of preferably 5-40 wt %, more preferably 5-20 wt %, of one tablet of the present invention.

The granule of the present invention may further contain an additive conventionally used in the field of pharmaceutical preparation. Examples of the additive include excipient, binder, colorant, pH adjusting agent, surfactant, stabilizer, acidulant, flavor, fluidizer, coating base, coating additive and the like. Unless particularly indicated, these additives are used in an amount conventionally employed in the field of pharmaceutical preparation.

Preferable examples of the excipient include mannitol; starches such as cornstarch, potato starch, wheat starch, rice starch, partly pregelatinized starch, pregelatinized starch, porous starch and the like; anhydrous calcium phosphate, precipitated calcium carbonate, calcium silicate and the like.

Mannitol is an excipient generally inducing a tableting trouble with ease. However, since the tablet of the present invention can prevent even a tableting trouble induced by mannitol, mannitol may be used for the purpose of improving the water solubility of the pharmaceutically active ingredient, improving the preservation stability of the pharmaceutically active ingredient and the like. For example, when compound A (or a salt thereof) is used as a pharmaceutically active ingredient, mannitol is preferably added as an excipient to the granule of the present invention to improve the preservation stability of compound A.

In the granule of the present invention, the excipient is used in an amount corresponding to the content of preferably 5-95 wt %, more preferably 30-80 wt %, of one tablet of the present invention.

Preferable examples of the binder include hydroxypropylcellulose, hydroxypropylmethylcellulose, polyvinylpyrrolidone (povidone), gum arabic and the like. Of these, hydroxypropylcellulose, polyvinylpyrrolidone and the like are preferable.

In the granule of the present invention, a binder is used in an amount corresponding to the content of preferably 1-20 wt %, more preferably 1-5 wt %, of one tablet of the present invention.

Preferable examples of the colorant include food colors such as Food Color Yellow No. 5, Food Color Red No. 2, Food Color Blue No. 2 and the like, food lake colors, red ferric oxide, yellow ferric oxide and the like.

Preferable examples of the pH adjusting agent include citrate, phosphate, carbonate, tartrate, fumarate, acetate, amino acid salt and the like.

Preferable examples of the surfactant include sodium lauryl sulfate, polysorbate 80, polyoxyethylene(160)polyoxypropylene(30)glycol and the like.

Preferable examples of the stabilizer include tocopherol, tetrasodium edetate, nicotinamide, cyclodextrins and the like.

Preferable examples of the acidulant include ascorbic acid, citric acid, tartaric acid, malic acid and the like.

Preferable examples of the flavor include menthol, peppermint oil, lemon oil, vanillin and the like.

Preferable examples of the fluidizer include light anhydrous silicic acid, hydrated silicon dioxide, talc and the like.

As preferable examples of the coating base, sugar coating base, aqueous film coating base, enteric film coating base, sustained-release film coating base and the like can be mentioned.

As the sugar coating base, sucrose is used, and one or more kinds selected from talc, precipitated calcium carbonate, gelatin, gum arabic, pullulan, carnauba wax and the like may be used in combination.

Examples of the aqueous film coating base include cellulose polymers such as hydroxypropylcellulose, hydroxypropylmethylcellulose (e.g., hypromellose 2910), hydroxyethylcellulose, methylhydroxyethylcellulose and the like; synthesis polymers such as polyvinyl acetaldiethylaminoacetate, aminoalkylmethacrylate copolymer E [Eudragit E (trade name)], polyvinylpyrrolidone and the like; polysaccharides such as pullulan and the like.

Examples of the enteric film coating base include cellulose polymers such as hydroxypropylmethylcellulose phthalate, hydroxypropylmethylcellulose acetatesuccinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like.

Examples of the sustained-release film coating base include cellulose polymers such as ethylcellulose and the like; acrylic acid polymers such as aminoalkyl methacrylate copolymer RS [Eudragit RS (trade name)], ethyl acrylate-methacrylic acid methyl copolymer suspension [Eudragit NE (trade name)] and the like.

Preferable examples of the coating additive include light shielding agent such as titanium oxide and the like; fluidizer such as talc and the like; colorant such as red ferric oxide, yellow ferric oxide and the like; plasticizers such as polyethylene glycol (e.g., macrogol 6000), triethyl citrate, castor oil, polysorbates and the like; organic acids such as citric acid, tartaric acid, malic acid, ascorbic acid and the like.

The above-mentioned additive may be a mixture of two or more kinds at an appropriate ratio.

The granule of the present invention is a composition preferably containing an excipient (preferably mannitol) and a binder (preferably hydroxypropylcellulose or povidone), in addition to the pharmaceutically active ingredient easily inducing a tableting trouble and microcrystalline cellulose.

The component (B) in the tablet of the present invention is a tableting aid comprising magnesium stearate and microcrystalline cellulose (hereinafter sometimes to be abbreviated as "the tableting aid of the present invention").

In the present specification, the "tableting aid" means an additive to be mixed with the aforementioned granule of the present invention before the tableting step during the production of the tablet of the present invention.

The magnesium stearate to be used as the tableting aid of the present invention is not particularly limited as long as it is used as an additive for pharmaceutical products.

In the tableting aid of the present invention, magnesium stearate is used in an amount corresponding to the content of preferably 0.5-2 wt %, more preferably 0.5-1.5 wt %, of one tablet of the present invention.

Examples of the microcrystalline cellulose to be used for the tableting aid of the present invention include those similar to the microcrystalline cellulose used for the aforementioned granule of the present invention. Here, the kind of the microcrystalline cellulose to be used for the granule and the kind of the microcrystalline cellulose to be used for the tableting aid may be the same or different.

In the tableting aid of the present invention, microcrystalline cellulose is used in an amount corresponding to the content of preferably 2-20 wt %, more preferably 2-15 wt %, of one tablet of the present invention.

The tableting aid of the present invention may further contain an additive conventionally used in the field of pharmaceutical preparation. Examples of the additive include the additives recited with regard to the above-mentioned granule and a disintegrant. Unless particularly indicated, these additives are used in an amount conventionally employed in the field of pharmaceutical preparation.

Preferable examples of the disintegrant include carboxymethylcellulose, calcium carboxymethylcellulose, sodium carboxymethyl starch, croscarmellose sodium, croscarmellose calcium, crospovidone, low-substituted hydroxypropylcellulose, hydroxypropylstarch and the like. Of these, croscarmellose sodium, carmellose calcium, low-substituted hydroxypropylcellulose and the like are preferable, and croscarmellose sodium is more preferable.

The tableting aid of the present invention is a composition preferably containing, besides magnesium stearate and microcrystalline cellulose, a disintegrant (preferably croscarmellose sodium, carmellose calcium or low-substituted hydroxypropylcellulose, more preferably, croscarmellose sodium) and, where necessary, a fluidizer (preferably light anhydrous silicic acid).

Here, the disintegrant is used in an amount corresponding to the content of preferably 1-15 wt %, more preferably 1-10 wt %, of one tablet of the present invention, and the fluidizer is used in an amount corresponding to the content of preferably 0.1-1.5 wt %, more preferably 0.5-1.0 wt %, of one tablet of the present invention.

The tablet of the present invention contains the granule of the present invention in an amount corresponding to the content of preferably 75-95 wt %, more preferably 80-90 wt %, of one tablet and the tableting aid of the present invention in an amount corresponding to the content of preferably 5-25 wt %, more preferably 10-20 wt %, of one tablet.

The tablet of the present invention contains microcrystalline cellulose of the granule of the present invention in an amount corresponding to the content of preferably 5-40 wt %, more preferably 5-20 wt %, of one tablet and microcrystalline cellulose of the tableting aid of the present invention in an amount corresponding to the content of preferably 2-20 wt %, more preferably 2-15 wt %, of one tablet.

Furthermore, the tablet of the present invention contains magnesium stearate in an amount corresponding to the content of preferably 0.5-2 wt %, more preferably 0.5-1.5 wt %, of the tableting aid of the present invention in one tablet.

Preferable specific examples of the tablet of the present invention include the following:
(Tablet A)
A tablet containing the following (A) and (B):
(A) a granule constituted with a pharmaceutically active ingredient easily inducing a tableting trouble (preferably compound A or a salt thereof (preferably benzoate)), microcrystalline cellulose, an excipient (preferably mannitol), and a binder (preferably hydroxypropylcellulose or povidone);
(B) a tableting aid constituted with magnesium stearate, microcrystalline cellulose, and a disintegrant (preferably croscarmellose sodium, carmellose calcium or low-substituted hydroxypropylcellulose, more preferably croscarmellose sodium) and, where necessary, a fluidizer (preferably light anhydrous silicic acid).

The tablet of the present invention may be film-coated from the aspects of easy administration, preparation strength and the like.

Preferable examples of the coating base and coating additive used for film coating include those similar to the ones used for the aforementioned granule of the present invention.

When the tablet of the present invention is film-coated, a film coating layer can be formed in a proportion of generally 1-10 parts by weight, preferably 2-6 parts by weight, per 100 parts by weight of the tablet of the present invention.

The tablet of the present invention can be produced by mixing (A) a granule comprising a pharmaceutically active ingredient easily inducing a tableting trouble and microcrystalline cellulose (i.e., the aforementioned "granule of the present invention") and (B) a tableting aid comprising magnesium stearate and microcrystalline cellulose (i.e., the aforementioned "tableting aid of the present invention"), and punching the mixture.

Specifically, the tablet of the present invention can be produced according to the following production steps. Each starting material used in the following production steps is used in such amount as to achieve the aforementioned content per finally obtained tablet.
1) The granule of the above-mentioned component (A) can be produced, for example, by uniformly mixing a pharmaceutically active ingredient easily inducing a tableting trouble and microcrystalline cellulose and, where necessary, an additive (excipient, preferably mannitol), and granulating the mixture. More specifically, granulation is performed while spraying a dispersion liquid of a binder (preferably hydroxypropylcellulose or povidone) in a solvent (e.g., water, acetone, ethyl alcohol, polyalcohol, and mixture thereof at appropriate ratio; when the pharmaceutically active ingredient is compound A, preferably water) in a fluidized bed granulation dryer. Then, the granule is dried, and the obtained granulated product is pulverized to give a sized powder.
2) As tableting aids, magnesium stearate, microcrystalline cellulose, components added as desired (preferably disintegrant (preferably croscarmellose sodium, carmellose calcium or low-substituted hydroxypropylcellulose, more preferably croscarmellose sodium), and a fluidizer (preferably light anhydrous silicic acid)) are added to and mixed with the sized powder to give a granule for tableting.
3) The granule is punched by a tableting machine to give a plain tablet.
4) When desired, a film coating solution is, for example, sprayed on the obtained plain tablet in a film coating machine to give film-coated tablets.

The above-mentioned dispersion liquid may be any of solution and suspension, and the "dispersion liquid" in the present specification includes both solution and suspension.

From the aspects of easy administration, preparation strength and the like, the tablet of the present invention is preferably film-coated. In addition, the above-mentioned tablet may be filled in a capsule (e.g., gelatin capsule) to give a capsule agent.

The tablet of the present invention may be stamped or printed with letters for discrimination, or have a score line for dividing the tablet.

The operations such as mixing, tableting, coating and the like in the aforementioned production step are performed according to a method conventionally used in the technical field of pharmaceutical preparations.

The mixing is performed, for example, using a mixer such as a V-type mixer, a tumbler mixer and the like; and a granulation machine such as a high speed mixer granulator, a fluidized bed granulation dryer, an extrusion granulator, a roller compactor and the like.

The tableting (punching) is performed, for example, using a single punch tableting machine, a rotary tableting machine and the like.

When a single punch tableting machine, a rotary tableting machine and the like are used, a tableting pressure of generally 1-45 $kN/cm^2$ (preferably 5-40 $kN/cm^2$) is preferably employed. Furthermore, to prevent capping, a tapered die is preferably used.

The coating is performed, for example, using a film coating apparatus and the like.

The solid preparation of the present invention preferably has a hardness of 70 to 200N.

The solid preparation of the present invention preferably dissolves out not less than 85% of the pharmaceutically active ingredient in 15 min when the tablet is subjected to a dissolution test according to the Paddle Method at 37° C., 50 rpm and using 0.01N hydrochloric acid; the Japanese Pharmacopoeia 2nd fluid (pH 6.8; pH 6.8, 0.1 mol/L phosphate buffer (mixture of equivalent volume of a solution obtained by dissolving 6.4 g of potassium dihydrogen phosphate and 18.9 g of disodium hydrogen phosphate 12 hydrate in 750 mL of water, adjusting to pH 6.8 with sodium hydroxide reagent, and adding water to 1000 mL) and water); purified water; 0.1 mol/L of hydrochloric acid; 0.25 mol/L of acetate buffer, pH 4.5; 0.05 mol/L of phosphate buffer, pH 6.8; or the like (representatively, 0.01N hydrochloric acid or the Japanese Pharmacopoeia 2nd fluid) as a test solution.

Here, the dissolution test is performed according to the method described in the Japanese Pharmacopoeia 15th edition.

The test solution can be prepared according to the Japanese Pharmacopoeia 15th edition. The amount of the test solution to be used is generally 900 mL.

The tablet of the present invention can be safely administered orally or parenterally to a mammal (e.g., mouse, rat, rabbit, cat, dog, bovine, horse, monkey, human).

The tablet of the present invention can be used for the prophylaxis, improvement or treatment of a disease or condition for which a component selected as a pharmaceutically active ingredient easily inducing a tableting trouble exerts efficacy.

As a specific example thereof, in the present invention, a tablet containing ibuprofen as a pharmaceutically active ingredient is useful, for example, for the reduction or treatment of pain, and the like.

In the present invention, a tablet containing vitamin C as the pharmaceutically active ingredient is useful, for example, as a prophylactic agent of scorbutus, supplement and the like.

In addition, in the present invention, a tablet containing trimebutine maleate as a pharmaceutically active ingredient is useful, for example, as a therapeutic agent for chronic gastritis, irritable bowel syndrome and the like, or an antiflatulent.

In the present invention, moreover, a tablet containing compound A (or a salt thereof) as a pharmaceutically active ingredient is useful for the prophylaxis or treatment of, for example, diabetes [e.g., type 1 diabetes, type 2 diabetes, type 1.5 diabetes (LADA (Latent Autoimmune Diabetes in Adults)), gestational diabetes, diabetes with impaired insulin secretion, obese diabetes, impaired glucose tolerance (IGT), IFG (Impaired Fasting Glucose), IFG (Impaired Fasting Glycaemia)], diabetic complications [e.g., neuropathy, nephropathy, retinopathy, cataract, macroangiopathy, arteriosclerosis, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], obesity, hyperlipidemia (e.g., hypertriglyceridemia, hypercholesterolemia, hypoHDL-emia, postprandial hyperlipemia), arteriosclerosis (e.g., atherosclerosis), hypertension, myocardial infarction, angina pectoris, cerebrovascular disorder (e.g., cerebral infarction, cerebral apoplexy), insulin resistance syndrome, syndrome X, dysmetabolic syndrome and the like.

In addition, a tablet containing compound A (or a salt thereof) is also useful for secondary prevention of the abovementioned various diseases (e.g., secondary prevention of cardiovascular event such as myocardial infarction and the like) or suppression of progression [e.g., suppression of progression from impaired glucose tolerance to diabetes; suppression of progression from diabetes to diabetic complications (preferably diabetic neuropathy, diabetic nephropathy, diabetic retinopathy, arteriosclerosis)].

The dose of the tablet of the present invention only needs to be an effective amount of the component selected as the pharmaceutically active ingredient easily inducing a tableting trouble to be contained in the tablet. In addition, while the administration frequency of the tablet of the present invention to the aforementioned mammal depends on the properties of the pharmaceutically active ingredient to be contained, it is typically 1 to 3 times a day.

In a specific example, an effective amount of compound A or a salt thereof is generally 0.01-1000 mg/day, preferably 1-50 mg/day, more preferably 3-25 mg/day, as compound A (free form), for example, for one adult (body weight 60 kg). Moreover, the administration frequency of the tablet containing compound A as a pharmaceutically active ingredient to the aforementioned mammal is preferably 1 to 3 times, more preferably once, a day.

Particularly preferable specific examples of the tablet containing compound A as a pharmaceutically active ingredient include
"a tablet containing 3.125 mg of compound A per tablet";
"a tablet containing 6.25 mg of compound A per tablet";
"a tablet containing 12.5 mg of compound A per tablet";
"a tablet containing 25 mg of compound A per tablet"; and
"a tablet containing 50 mg of compound A per tablet".

The tablet of the present invention and the pharmaceutically active ingredient easily inducing a tableting trouble contained in the tablet can be used in combination with one or more other kinds of pharmaceutical agents (hereinafter sometimes to be abbreviated as a concomitant drug).

Specific examples thereof include a combined use of compound A (or a salt thereof) and one or more pharmaceutical agents selected from a therapeutic agent for diabetes, a therapeutic agent for diabetic complications, a therapeutic agent for hyperlipidemia, an antihypertensive agent, an antiobestic agent, a diuretic, an antithrombotic agent and the like (hereinafter sometimes to be abbreviated as concomitant drug of compound A).

Examples of the therapeutic agent for diabetes include insulin preparations (e.g., animal insulin preparation extracted from the pancreas of bovine, swine; human insulin preparation synthesized by genetic engineering using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), tesaglitazar, Ragaglitazar, muraglitazar, edaglitazone, metaglidasen, Naveglitazar, AMG-131, THR-0921), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate], dipeptidyl peptidase IV inhibitors other than compound A (e.g., Vildagliptin, sitagliptin, saxagliptin, T-6666, TS-021), β3 agonists (e.g., AJ-9677), GPR40 agonists, GLP-1 receptor agonists [e.g., GLP-1, GLP-1MR agent, N,N-2211, AC-2993 (exendin-4), BIM-51077, Aib(8, 35)hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitor, glucose-6-phosphatase inhibitor, glucagon antagonist), SGLUT (sodium-glucose cotransporter) inhibitors (e.g., T-1095), 11β-hydroxysteroid dehydrogenase inhibitors (e.g., BVT-3498), adiponectin or agonist thereof, IKK inhibitors (e.g., AS-2868), leptin resistance improving drugs, somatostatin receptor agonists, glucokinase activators (e.g., Ro-28-1675), GIP (glucose-dependent insulinotropic peptide) and the like.

Examples of the therapeutic agents for diabetic complications include aldose reductase inhibitors (e.g., tolrestat, epalrestat, zenarestat, zopolrestat, minalrestat, fidarestat, CT-112), neurotrophic factors and increasing drugs thereof (e.g., NGF, NT-3, BDNF, neurotrophin production/secretion promoting agent described in WO01/14372 (e.g., 4-(4-chlorophenyl)-2-(2-methyl-1-imidazolyl)-5-[3-(2-methylphenoxy)propyl]oxazole)), nerve regeneration promoters (e.g., Y-128), PKC inhibitors (e.g., ruboxistaurin mesylate), AGE inhibitors (e.g., ALT946, pimagedine, N-phenacylthiazolium bromide (ALT766), ALT-711, EXO-226, Pyridorin, pyridoxamine), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

Examples of the therapeutic agent for hyperlipidemia include HMG-CoA reductase inhibitors (e.g., pravastatin, simvastatin, lovastatin, atorvastatin, fluvastatin, pitavastatin, rosuvastatin or salts thereof (e.g., sodium salt, calcium salt)), squalene synthase inhibitors (e.g., lapaquistat acetate), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterol (e.g., soysterol, γ-oryzanol) and the like.

Examples of the antihypertensive agent include angiotensin converting enzyme inhibitors (e.g., captopril, enalapril, delapril), angiotensin II receptor antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobestic agent include antiobestic agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonist), pancreatic lipase inhibitors (e.g., orlistat, cetilistat), β3 agonists (e.g., AJ-9677), anorectic peptides (e.g., leptin, CNTF (ciliary neurotrophic factor)), cholecystokinin agonists (e.g., lintitript, FPL-15849), feeding deterrents (e.g., P-57) and the like.

Examples of the diuretic include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparins (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Of the above-mentioned concomitant drugs of compound A, insulin sensitizers (preferably pioglitazone hydrochloride), insulin preparation, α-glucosidase inhibitors (preferably voglibose, acarbose), biguanides (preferably metformin hydrochloride), sulfonylureas (preferably glimepiride) and the like are preferable.

When the tablet of the present invention and a concomitant drug are used in combination, the administration time of these is not limited, and the tablet of the present invention and the concomitant drug may be administered simultaneously to an administration subject, or may be administered in a staggered manner.

In addition, the tablet of the present invention and the combination drug may be administered as separate preparations to an administration subject, or the tablet of the present invention and the combination drug may be administered to an administration subject as a single preparation containing the tablet of the present invention and the concomitant drug.

The dose of the concomitant drug can be appropriately determined based on the clinically employed dose of each drug. In addition, the mixing ratio of the tablet of the present invention and the concomitant drug can be appropriately determined according to the administration subject, administration route, target disease, condition, combination and the like. For example, when the administration subject is a human, the concomitant drug may be used in an amount of 0.01 to 100 parts by weight per 1 part by weight of the tablet of the present invention.

Use of the concomitant drug in this way provides superior effects such as 1) enhanced action of the tablet of the present invention or the concomitant drug (synergistic effect of the actions of the pharmaceutical agents), 2) reduced dose of the tablet of the present invention or the concomitant drug (effect of reduction of dose of pharmaceutical agents as compared to single drug administration), 3) reduced secondary action of the tablet of the present invention or the concomitant drug, and the like.

The present invention is explained in more detail in the following by referring to Comparative Example, Example and Experimental Examples, which are not to be construed as limitative.

As additives for pharmaceutical preparations in the following Comparative Examples and Examples, the Japanese Pharmacopoeia 15th edition, the Japanese Pharmacopoeia Japanese Pharmaceutical Codex or Japanese Pharmaceutical Excipients 2003 compatible products were used.

EXAMPLES

Comparative Example 1

Benzoate of compound A, mannitol and microcrystalline cellulose according to the formulation of Table 1 were uniformly mixed in a fluidized bed granulation dryer (LAB-1, POWREX CORPORATION), and the mixture was granulated by spraying an aqueous solution of hydroxypropylcellulose and dried therein. The obtained granules were passed through a sieve (16M) to give a sized powder. To the sized powder were added croscarmellose sodium and magnesium stearate, and they were mixed in a bag to give granules for tableting. The granules were punched by a rotary tableting machine (Correct 19K, Kikusui Seisakusho, Ltd.) with a 8.5 mmφ punch to give a plain tablet weighting 250 mg. A hypromellose 2910 solution obtained by dispersing titanium oxide was sprayed on the obtained plain tablet in a film coating machine (Hicoater HCP-75, Freund Corporation) to give a film-coated tablet containing 12.5 mg of compound A (free form) per tablet and a film-coated tablet containing 50 mg of compound A (free form) per tablet. Sticking was observed in the production of Comparative Example.

TABLE 1

|  |  | dose | |
|---|---|---|---|
|  |  | 12.5 mg | 50 mg |
|  | plain tablet | | |
| component (A) | compound A (benzoate) | 17.00 mg | 68.00 mg |
|  | mannitol | 171.50 mg | 120.50 mg |
|  | microcrystalline cellulose | 37.50 mg | 37.50 mg |
|  | hydroxypropylcellulose | 6.50 mg | 6.50 mg |
| component (B) | croscarmellose sodium | 15.00 mg | 15.00 mg |
|  | magnesium stearate | 2.50 mg | 2.50 mg |
|  | film coating | | |
|  | hypromellose 2910 | 7.20 mg | 7.20 mg |
|  | titanium oxide | 0.80 mg | 0.80 mg |
|  | total | 258.00 mg | 258.00 mg |

Example 1

Benzoate of compound A, mannitol and microcrystalline cellulose according to the formulation of Table 2 were uniformly mixed in a fluidized bed granulation dryer (LAB-1, POWREX CORPORATION), and the mixture was granulated by spraying an aqueous solution of hydroxypropylcellulose and dried therein. The obtained granules were passed through a sieve (16M) to give a sized powder. To the sized powder were added microcrystalline cellulose, croscarmellose sodium, light anhydrous silicic acid and magnesium stearate, and they were mixed in a bag to give granules for tableting. The granules were punched by a rotary tableting machine (Correct 19K, Kikusui Seisakusho, Ltd.) with a 14.6 mm×5.6 mm oblong punch to give a plain tablet weighting 300 mg. A hypromellose 2910 solution obtained by dispersing titanium oxide and yellow ferric oxide or red ferric oxide was sprayed on the obtained plain tablet in a film coating machine (Hicoater HCP-75, Freund Corporation) to give a film-coated tablet containing 12.5 mg of compound A (free form) per tablet and a film-coated tablet containing 50 mg of compound A (free form) per tablet. A tableting trouble was not observed in this Example.

TABLE 2

|  |  | dose | |
|---|---|---|---|
|  |  | 12.5 mg | 50 mg |
| plain tablet | | | |
| component (A) | compound A (benzoate) | 17.00 mg | 68.00 mg |
|  | mannitol | 208.60 mg | 157.60 mg |
|  | microcrystalline cellulose | 30.00 mg | 30.00 mg |
|  | hydroxypropylcellulose | 9.00 mg | 9.00 mg |
| component (B) | microcrystalline cellulose | 15.00 mg | 15.00 mg |
|  | croscarmellose sodium | 15.00 mg | 15.00 mg |
|  | light anhydrous silicic acid | 2.40 mg | 2.40 mg |
|  | magnesium stearate | 3.00 mg | 3.00 mg |
| film coating | | | |
|  | hypromellose 2910 | 8.01 mg | 8.01 mg |
|  | titanium oxide | 0.90 mg | 0.90 mg |
|  | yellow ferric oxide | 0.09 mg | — mg |
|  | red ferric oxide | — mg | 0.09 mg |
|  | total | 309.00 mg | 309.00 mg |

Example 2

Benzoate of compound A, mannitol and microcrystalline cellulose according to the formulation of Table 3 were uniformly mixed in a fluidized bed granulation dryer (LAB-1, POWREX CORPORATION), and the mixture was granulated by spraying an aqueous solution of hydroxypropylcellulose and dried therein. The obtained granules were passed through a sieve (16M) to give a sized powder. To the sized powder were added microcrystalline cellulose, croscarmellose sodium, light anhydrous silicic acid and magnesium stearate, and they were mixed in a bag to give granules for tableting. The granules were punched by a compact rotary tableting machine (VEL5, Kikusui Seisakusho, Ltd.) with a 9.0 mm×5.0 mm oval punch to give a plain tablet weighting 150 mg. A hypromellose 2910 solution obtained by dispersing titanium oxide and yellow ferric oxide or red ferric oxide was sprayed on the obtained plain tablet in a film coating machine (Hicoater HCP-75, Freund Corporation) to give a film-coated tablet containing 12.5 mg of compound A (free form) per tablet and a film-coated tablet containing 25 mg of compound A (free form) per tablet. A tableting trouble was not observed in this Example.

TABLE 3

|  |  | dose | |
|---|---|---|---|
|  |  | 12.5 mg | 25 mg |
| plain tablet | | | |
| component (A) | compound A (benzoate) | 17.00 mg | 34.00 mg |
|  | mannitol | 95.80 mg | 78.80 mg |
|  | microcrystalline cellulose | 15.00 mg | 15.00 mg |
|  | hydroxypropylcellulose | 4.50 mg | 4.50 mg |
| component (B) | microcrystalline cellulose | 7.50 mg | 7.50 mg |
|  | croscarmellose sodium | 7.50 mg | 7.50 mg |
|  | light anhydrous silicic acid | 1.20 mg | 1.20 mg |
|  | magnesium stearate | 1.50 mg | 1.50 mg |
| film coating | | | |
|  | hypromellose 2910 | 5.34 mg | 5.34 mg |
|  | titanium oxide | 0.60 mg | 0.60 mg |
|  | yellow ferric oxide | 0.06 mg | — mg |
|  | red ferric oxide | — mg | 0.06 mg |
|  | total | 156.00 mg | 156.00 mg |

Example 3

Benzoate of compound A, mannitol and microcrystalline cellulose according to the formulation of Table 4 were uniformly mixed in a fluidized bed granulation dryer (FD-5S, POWREX CORPORATION), and the mixture was granulated by spraying an aqueous solution of hydroxypropylcellulose and dried therein. The obtained granules were pulverized by a powermill grinder (P-3, Showa Chemical Machinery) using a 1.5 mmϕ punching screen. To the obtained sized powder were added microcrystalline cellulose, croscarmellose sodium and magnesium stearate, and they were mixed in a tumbler mixer (TM-15, Showa Chemical Machinery) to give granules for tableting. The granules were punched by a rotary tableting machine (Correct 12HUK, Kikusui Seisakusho, Ltd.) with a 9.0 mm×5.0 mm oval punch to give a plain tablet weighting 150 mg. A hypromellose 2910 solution obtained by dispersing titanium oxide and yellow ferric oxide or red ferric oxide was sprayed on the obtained plain tablet in a film coating machine (DRC-650, POWREX CORPORATION), and a macrogol 6000 solution was successively sprayed thereon to give a film-coated tablet containing 12.5 mg of compound A (free form) per tablet and a film-coated tablet containing 25 mg of compound A (free form) per tablet. A tableting trouble was not observed in this Example.

TABLE 4

|  |  | dose | |
|---|---|---|---|
|  |  | 12.5 mg | 25 mg |
| plain tablet | | | |
| component (A) | compound A (benzoate) | 17.00 mg | 34.00 mg |
|  | mannitol | 96.70 mg | 79.70 mg |
|  | microcrystalline cellulose | 15.00 mg | 15.00 mg |
|  | hydroxypropylcellulose | 4.50 mg | 4.50 mg |

TABLE 4-continued

|  |  | dose | |
|---|---|---|---|
|  |  | 12.5 mg | 25 mg |
| component (B) | microcrystalline cellulose | 7.50 mg | 7.50 mg |
|  | croscarmellose sodium | 7.50 mg | 7.50 mg |
|  | magnesium stearate | 1.80 mg | 1.80 mg |
| film coating | | | |
|  | hypromellose 2910 | 5.34 mg | 5.34 mg |
|  | titanium oxide | 0.60 mg | 0.60 mg |
|  | yellow ferric oxide | 0.06 mg | — mg |
|  | red ferric oxide | — mg | 0.06 mg |
|  | macrogol 6000 | 0.1 mg | 0.1 mg |
|  | total | 156.10 mg | 156.10 mg |

Example 4

Benzoate of compound A, mannitol and microcrystalline cellulose according to the formulation of Table 4 and the amount of charge shown in Table 5 were uniformly mixed in a fluidized bed granulation dryer (FD-WSG-60, POWREX CORPORATION), and the mixture was granulated by spraying an aqueous solution of hydroxypropylcellulose and dried therein. The obtained granules were pulverized by a powermill grinder (P-7S, Showa Chemical Machinery) using a 1.5 mmφ punching screen. To the obtained sized powder were added microcrystalline cellulose, croscarmellose sodium and magnesium stearate, and they were mixed in a tumbler mixer (TM-400S, Showa Chemical Machinery) to give granules for tableting. The granules were punched by a rotary tableting machine (AQUA0836SS2JII, Kikusui Seisakusho, Ltd.) with a 9.0 mm×5.0 mm oval punch to give a plain tablet weighting 150 mg. A hypromellose 2910 solution obtained by dispersing titanium oxide and yellow ferric oxide or red ferric oxide was sprayed on the obtained plain tablet in a film coating machine (DRC-1200, POWREX CORPORATION), and a macrogol 6000 solution was successively sprayed thereon to give a film-coated tablet containing 12.5 mg of compound A (free form) per tablet and a film-coated tablet containing 25 mg of compound A (free form) per tablet. A tableting trouble was not observed in this Example.

TABLE 5

|  |  | dose | |
|---|---|---|---|
|  |  | 12.5 mg | 25 mg |
| plain tablet | | | |
| component (A) | hydroxypropylcellulose | 2025 g | 2025 g |
|  | purified water | 31725 g | 31725 g |
|  | compound A (benzoate) | 7650 g | 15300 g |
|  | mannitol | 43515 g | 35865 g |
|  | microcrystalline cellulose | 6750 g | 6750 g |
| component (B) | microcrystalline cellulose | 3375 g | 3375 g |
|  | croscarmellose sodium | 3375 g | 3375 g |
|  | magnesium stearate | 810.0 g | 810.0 g |
| film coating | | | |
|  | hypromellose 2910 | 4007 g | 4007 g |
|  | titanium oxide | 450.2 g | 450.2 g |
|  | yellow ferric oxide | 45.02 g | — g |
|  | red ferric oxide | — g | 45.02 g |

TABLE 5-continued

|  |  | dose | |
|---|---|---|---|
|  |  | 12.5 mg | 25 mg |
|  | purified water | 40523 g | 40523 g |
|  | macrogol 6000 | 1842 g | 1842 g |
|  | purified water | 16580 g | 16580 g |

Example 5

Benzoate of compound A, mannitol and microcrystalline cellulose according to the formulation of Table 6 were uniformly mixed in a fluidized bed granulation dryer (FD-5S, POWREX CORPORATION), and the mixture was granulated by spraying an aqueous solution of hydroxypropylcellulose and dried therein. The obtained granules were pulverized by a powermill grinder (P-3, Showa Chemical Machinery) using a 1.5 mmφ punching screen. To the obtained sized powder were added microcrystalline cellulose, croscarmellose sodium and magnesium stearate, and they were mixed in a tumbler mixer (TM-15, Showa Chemical Machinery) to give granules for tableting. The granules were punched by a rotary tableting machine (Correct 12HUK, Kikusui Seisakusho, Ltd.) with a 9.0 mm×5.0 mm oval punch to give a plain tablet weighting 150 mg. A hypromellose 2910 solution obtained by dispersing titanium oxide and yellow ferric oxide or red ferric oxide was sprayed on the obtained plain tablet in a film coating machine (Hicoater HCP-75, Freund Corporation) to give a film-coated tablet containing 12.5 mg of compound A (free form) per tablet and a film-coated tablet containing 25 mg of compound A (free form) per tablet. A tableting trouble was not observed in this Example.

TABLE 6

|  |  | dose | |
|---|---|---|---|
|  |  | 12.5 mg | 25 mg |
| plain tablet | | | |
| component (A) | compound A(benzoate) | 17.00 mg | 34.00 mg |
|  | mannitol | 96.70 mg | 79.70 mg |
|  | microcrystalline cellulose | 15.00 mg | 15.00 mg |
|  | hydroxypropylcellulose | 4.50 mg | 4.50 mg |
| component (B) | microcrystalline cellulose | 7.50 mg | 7.50 mg |
|  | croscarmellose sodium | 7.50 mg | 7.50 mg |
|  | magnesium stearate | 1.80 mg | 1.80 mg |
| film coating | | | |
|  | hypromellose 2910 | 5.37 mg | 5.388 mg |
|  | titanium oxide | 0.60 mg | 0.600 mg |
|  | yellow ferric oxide | 0.03 mg | — |
|  | red ferric oxide | — | 0.012 mg |
|  | total | 156.00 mg | 156.00 mg |

Example 6

Benzoate of compound A, mannitol and microcrystalline cellulose according to the formulation of Table 7 were uniformly mixed in a fluidized bed granulation dryer (LAB-1, POWREX CORPORATION), and the mixture was granulated by spraying an aqueous solution of povidone and dried therein. The obtained granules were passed through a sieve (16M) to give a sized powder. To the sized powder were added microcrystalline cellulose, croscarmellose sodium and magnesium stearate, and they were mixed in a bag to give granules for tableting. The granules were punched by a compact rotary tableting machine (VEL5, Kikusui Seisakusho, Ltd.) with a 9.0 mm×5.0 mm oval punch to give a plain tablet weighting 150 mg. A hypromellose 2910 solution obtained by dispersing titanium oxide was sprayed on the obtained plain tablet in a film coating machine (Hicoater HCP-75, Freund Corporation), and a macrogol 6000 solution was successively sprayed thereon to give a film-coated tablet containing 12.5 mg of compound A (free form) per tablet and a film-coated tablet containing 25 mg of compound A (free form) per tablet. A tableting trouble was not observed in this Example.

TABLE 7

|  |  | dose | |
|---|---|---|---|
|  |  | 12.5 mg | 25 mg |
| plain tablet | | | |
| component (A) | compound A (benzoate) | 17.00 mg | 34.00 mg |
|  | mannitol | 96.70 mg | 79.70 mg |
|  | microcrystalline cellulose | 15.00 mg | 15.00 mg |
|  | povidone | 4.50 mg | 4.50 mg |
| component (B) | microcrystalline cellulose | 7.50 mg | 7.50 mg |
|  | croscarmellose sodium | 7.50 mg | 7.50 mg |
|  | magnesium stearate | 1.80 mg | 1.80 mg |
| film coating | | | |
|  | hypromellose 2910 | 5.40 mg | 5.40 mg |
|  | titanium oxide | 0.60 mg | 0.60 mg |
|  | macrogol 6000 | 0.1 mg | 0.1 mg |
|  | total | 156.10 mg | 156.10 mg |

Example 7

Benzoate of compound A, mannitol and microcrystalline cellulose according to the formulation of Table 8 were uniformly mixed in a fluidized bed granulation dryer (LAB-1, POWREX CORPORATION), and the mixture was granulated by spraying an aqueous solution of hydroxypropylcellulose and dried therein. The obtained granules were passed through a sieve (16M) to give a sized powder. To the sized powder were added microcrystalline cellulose, croscarmellose sodium and magnesium stearate, and they were mixed in a bag to give granules for tableting. The granules were punched by a rotary tableting machine (Correct 19K, Kikusui Seisakusho, Ltd.) with a 7.5 mmφ punch to give a plain tablet weighting 150 mg. A hypromellose 2910 solution obtained by dispersing titanium oxide and red ferric oxide was sprayed on the obtained plain tablet in a film coating machine (Hicoater HCP-75, Freund Corporation) to give a film-coated tablet containing 6.25 mg of compound A (free form) per tablet and a film-coated tablet containing 50 mg of compound A (free form) per tablet. A tableting trouble was not observed in this Example.

TABLE 8

|  |  | dose | |
|---|---|---|---|
|  |  | 6.25 mg | 50 mg |
| plain tablet | | | |
| component (A) | compound A (benzoate) | 8.50 mg | 68.00 mg |
|  | mannitol | 105.20 mg | 45.70 mg |
|  | microcrystalline cellulose | 15.00 mg | 15.00 mg |
|  | hydroxypropylcellulose | 4.50 mg | 4.50 mg |
| component (B) | microcrystalline cellulose | 7.50 mg | 7.50 mg |
|  | croscarmellose sodium | 7.50 mg | 7.50 mg |
|  | magnesium stearate | 1.80 mg | 1.80 mg |
| film coating | | | |
|  | hypromellose 2910 | 5.388 mg | 5.388 mg |
|  | titanium oxide | 0.600 mg | 0.600 mg |
|  | red ferric oxide | 0.012 mg | 0.012 mg |
|  | total | 156.00 mg | 156.00 mg |

Example 8

Benzoate of compound A, mannitol and microcrystalline cellulose according to the formulation of Table 9 were uniformly mixed in a fluidized bed granulation dryer (FD-5S, POWREX CORPORATION), and the mixture was granulated by spraying an aqueous solution of hydroxypropylcellulose and dried therein. The obtained granules were pulverized by a powermill grinder (P-3, Showa Chemical Machinery) using a 1.5 mmφ punching screen. To the obtained sized powder were added microcrystalline cellulose, croscarmellose sodium and magnesium stearate, and they were mixed in a tumbler mixer (TM-15, Showa Chemical Machinery) to give granules for tableting. The granules were punched by a rotary tableting machine (Correct 19K, Kikusui Seisakusho, Ltd.) with a 7.5 mmφ punch to give a plain tablet weighting 150 mg. A hypromellose 2910 solution obtained by dispersing titanium oxide and red ferric oxide was sprayed on the obtained plain tablet in a film coating machine (DRC-500, POWREX CORPORATION) to give a film-coated tablets (formulation A and formulation B) containing 6.25 mg of compound A (free form) per tablet. A tableting trouble was not observed in this Example.

TABLE 9

|  |  | dose | |
|---|---|---|---|
|  |  | 6.25 mg | 6.25 mg |
|  |  | formulation | |
|  |  | formulation A | formulation B |
| plain tablet | | | |
| component (A) | compound A (benzoate) | 8.50 mg | 8.50 mg |
|  | mannitol | 105.20 mg | 105.20 mg |
|  | microcrystalline cellulose | 15.00 mg | 7.50 mg |
|  | hydroxypropyl-cellulose | 4.50 mg | 4.50 mg |

TABLE 9-continued

| | | dose | |
|---|---|---|---|
| | | 6.25 mg | 6.25 mg |
| | | formulation | |
| | | formulation A | formulation B |
| component (B) | microcrystalline cellulose | 7.50 mg | 15.00 mg |
| | croscarmellose sodium | 7.50 mg | 7.50 mg |

TABLE 9-continued

| | dose | |
|---|---|---|
| | 6.25 mg | 6.25 mg |
| | formulation | |
| | formulation A | formulation B |
| magnesium stearate | 1.80 mg | 1.80 mg |
| film coating | | |
| hypromellose 2910 | 5.388 mg | 5.388 mg |
| titanium oxide | 0.600 mg | 0.600 mg |
| red ferric oxide | 0.012 mg | 0.012 mg |
| total | 156.00 mg | 156.00 mg |

Example 9

Benzoate of compound A, mannitol and microcrystalline cellulose according to the formulation of Table 10 and the amount of charge shown in Table 11 were uniformly mixed in a fluidized bed granulation dryer (FD-WSG-60, POWREX CORPORATION), and the mixture was granulated by spraying an aqueous solution of hydroxypropylcellulose and dried therein. The obtained granules were pulverized by a power-mill grinder (P-7S, Showa Chemical Machinery) using a 1.5 mmϕ punching screen. To the obtained sized powder were added microcrystalline cellulose, croscarmellose sodium and magnesium stearate, and they were mixed in a tumbler mixer (TM-400S, Showa Chemical Machinery) to give granules for tableting. The granules were punched by a rotary tableting machine (AQUA0836SS2JII, Kikusui Seisakusho, Ltd.) with a 7.5 mmϕ punch to give a plain tablet weighting 150 mg. A hypromellose 2910 solution obtained by dispersing titanium oxide and red ferric oxide was sprayed on the obtained plain tablet in a film coating machine (DRC-1200, POWREX CORPORATION) to give a film-coated tablet containing 6.25 mg of compound A (free form) per tablet, a film-coated tablet containing 12.5 mg of compound A (free form) per tablet and a film-coated tablet containing 25 mg of compound A (free form) per tablet. A tableting trouble was not observed in this Example.

TABLE 10

| dose | | 6.25 mg | 12.5 mg | 25 mg |
|---|---|---|---|---|
| | | plain tablet | | |
| component (A) | compound A (benzoate) | 8.50 mg | 17.00 mg | 34.00 mg |
| | mannitol | 105.20 mg | 96.70 mg | 79.70 mg |
| | microcrystalline cellulose | 15.00 mg | 15.00 mg | 15.00 mg |
| | hydroxypropylcellulose | 4.50 mg | 4.50 mg | 4.50 mg |
| component (B) | microcrystalline cellulose | 7.50 mg | 7.50 mg | 7.50 mg |
| | croscarmellose sodium | 7.50 mg | 7.50 mg | 7.50 mg |
| | magnesium stearate | 1.80 mg | 1.80 mg | 1.80 mg |
| | | film coating | | |
| | hypromellose 2910 | 5.388 mg | 5.388 mg | 5.388 mg |
| | titanium oxide | 0.600 mg | 0.600 mg | 0.600 mg |
| | red ferric oxide | 0.012 mg | 0.012 mg | 0.012 mg |
| | total | 156.00 mg | 156.00 mg | 156.00 mg |

TABLE 11

| dose | | 6.25 mg | 12.5 mg | 25 mg |
|---|---|---|---|---|
| | | plain tablet | | |
| component (A) | hydroxypropylcellulose | 2025 g | 2025 g | 2025 g |
| | purified water | 31725 g | 31725 g | 31725 g |
| | compound A (benzoate) | 3825 g | 7650 g | 15300 g |
| | mannitol | 47340 g | 43515 g | 35865 g |
| | microcrystalline cellulose | 6750 g | 6750 g | 6750 g |
| component (B) | microcrystalline cellulose | 3375 g | 3375 g | 3375 g |
| | croscarmellose sodium | 3375 g | 3375 g | 3375 g |
| | magnesium stearate | 810.0 g | 810.0 g | 810.0 g |
| | | film coating | | |
| | hypromellose 2910 | 4043 g | 4043 g | 4043 g |
| | titanium oxide | 450.2 g | 450.2 g | 450.2 g |
| | red ferric oxide | 9.004 g | 9.004 g | 9.004 g |
| | purified water | 40523 g | 40523 g | 40523 g |

Example 10

Benzoate of compound A, mannitol and microcrystalline cellulose according to the formulation of Table 12 were uniformly mixed in a fluidized bed granulation dryer (FD-5S, POWREX CORPORATION), and the mixture was granulated by spraying an aqueous solution of hydroxypropylcellulose and dried therein. The obtained granules were pulverized by a powermill grinder (P-3, Showa Chemical Machinery) using a 1.5 mmφ punching screen. To the obtained sized powder were added microcrystalline cellulose, croscarmellose sodium and magnesium stearate, and they were mixed in a tumbler mixer (TM-15, Showa Chemical Machinery) to give granules for tableting. The granules were punched by a rotary tableting machine (Correct 12HUK, Kikusui Seisakusho, Ltd.) with a 9.0 mm×5.0 mm oval punch to give a plain tablet weighting 150 mg. A hypromellose 2910 solution obtained by dispersing titanium oxide and yellow ferric oxide or red ferric oxide was sprayed on the obtained plain tablet in a film coating machine (DRC-500, POWREX CORPORATION), and a macrogol 6000 solution was successively sprayed thereon to give a film-coated tablet containing 3.125 mg of compound A (free form) per tablet and a film-coated tablet containing 6.25 mg of compound A (free form) per tablet. A tableting trouble was not observed in this Example.

TABLE 12

|  |  | dose | |
|---|---|---|---|
|  |  | 3.125 mg | 6.25 mg |
| plain tablet | | | |
| component (A) | compound A (benzoate) | 4.25 mg | 8.50 mg |
|  | mannitol | 109.45 mg | 105.20 mg |
|  | microcrystalline cellulose | 15.00 mg | 15.00 mg |
|  | hydroxypropylcellulose | 4.50 mg | 4.50 mg |
| component (B) | microcrystalline cellulose | 7.50 mg | 7.50 mg |
|  | croscarmellose sodium | 7.50 mg | 7.50 mg |
|  | magnesium stearate | 1.80 mg | 1.80 mg |
| film coating | | | |
|  | hypromellose 2910 | 5.388 mg | 5.388 mg |
|  | titanium oxide | 0.60 mg | 0.60 mg |
|  | yellow ferric oxide | 0.012 mg | — mg |
|  | red ferric oxide | — mg | 0.012 mg |
|  | macrogol 6000 | 0.1 mg | 0.1 mg |
|  | total | 156.10 mg | 156.10 mg |

Example 11

Benzoate of compound A, mannitol and microcrystalline cellulose according to the formulation of Table 13 and the amount of charge shown in Table 14 were uniformly mixed in a fluidized bed granulation dryer (FD-WSG-60, POWREX CORPORATION), and the mixture was granulated by spraying an aqueous solution of hydroxypropylcellulose and dried therein. The obtained granules were pulverized by a powermill grinder (P-7S, Showa Chemical Machinery) using a 1.5 mmφ punching screen. To the obtained sized powder were added microcrystalline cellulose, croscarmellose sodium and magnesium stearate, and they were mixed in a tumbler mixer (TM-400S, Showa Chemical Machinery) to give granules for tableting. The granules were punched by a rotary tableting machine (AQUA0836SS2JII, Kikusui Seisakusho, Ltd.) with a 9.0 mm×5.0 mm oval punch to give a plain tablet weighting 150 mg. A hypromellose 2910 solution obtained by dispersing titanium oxide and yellow ferric oxide or red ferric oxide was sprayed on the obtained plain tablet in a film coating machine (DRC-1200, POWREX CORPORATION), and a macrogol 6000 solution was successively sprayed thereon to give a film-coated tablet containing 3.125 mg of compound A (free form) per tablet and a film-coated tablet containing 6.25 mg of compound A (free form) per tablet. A tableting trouble was not observed in this Example.

TABLE 13

|  |  | dose | |
|---|---|---|---|
|  |  | 3.125 mg | 6.25 mg |
| plain tablet | | | |
| component (A) | compound A (benzoate) | 4.25 mg | 8.50 mg |
|  | mannitol | 109.45 mg | 105.20 mg |
|  | microcrystalline cellulose | 15.00 mg | 15.00 mg |
|  | hydroxypropylcellulose | 4.50 mg | 4.50 mg |
| component (B) | microcrystalline cellulose | 7.50 mg | 7.50 mg |
|  | croscarmellose sodium | 7.50 mg | 7.50 mg |
|  | magnesium stearate | 1.80 mg | 1.80 mg |
| film coating | | | |
|  | hypromellose 2910 | 5.388 mg | 5.388 mg |
|  | titanium oxide | 0.60 mg | 0.60 mg |
|  | yellow ferric oxide | 0.012 mg | — mg |
|  | red ferric oxide | — mg | 0.012 mg |
|  | macrogol 6000 | 0.1 mg | 0.1 mg |
|  | total | 156.10 mg | 156.10 mg |

TABLE 14

|  |  | dose | |
|---|---|---|---|
|  |  | 3.125 mg | 6.25 mg |
| plain tablet | | | |
| component (A) | hydroxypropylcellulose | 2025 g | 2025 g |
|  | purified water | 31725 g | 31725 g |
|  | compound A (benzoate) | 1913 g | 3825 g |
|  | mannitol | 49253 g | 47340 g |
|  | microcrystalline cellulose | 6750 g | 6750 g |
| component (B) | microcrystalline cellulose | 3375 g | 3375 g |
|  | croscarmellose sodium | 3375 g | 3375 g |
|  | magnesium stearate | 810.0 g | 810.0 g |
| film coating | | | |
|  | hypromellose 2910 | 4043 g | 4043 g |
|  | titanium oxide | 450.2 g | 450.2 g |
|  | yellow ferric oxide | 9.004 g | — g |
|  | red ferric oxide | — g | 9.004 g |
|  | purified water | 40523 g | 40523 g |
|  | macrogol 6000 | 1842 g | 1842 g |
|  | purified water | 16580 g | 16580 g |

Example 12

Benzoate of compound A, mannitol and microcrystalline cellulose according to the formulation of Table 15 and the amount of charge shown in Table 16 were uniformly mixed in a fluidized bed granulation dryer (FD-WSG-60, POWREX CORPORATION), and the mixture was granulated by spraying an aqueous solution of hydroxypropylcellulose and dried therein. The obtained granules were pulverized by a powermill grinder (P-7S, Showa Chemical Machinery) using a 1.5 mmφ punching screen. To the obtained sized powder were added microcrystalline cellulose, croscarmellose sodium and magnesium stearate, and they were mixed in a tumbler mixer (TM-400S, Showa Chemical Machinery) to give granules for tableting. The granules were punched by a rotary tableting machine (AQUA0836SS2JII, Kikusui Seisakusho, Ltd.) with a 10.0 mm×5.0 mm oval punch with or without a score line to give a plain tablet weighting 150 mg. A hypromellose 2910 solution obtained by dispersing titanium oxide and yellow ferric oxide or red ferric oxide was sprayed on the obtained plain tablet in a film coating machine (DRC-1200, POWREX CORPORATION), and a macrogol 6000 solution was successively sprayed thereon to give a film-coated tablet containing 3.125 mg of compound A (free form) per tablet, a film-coated tablet with a score line on both surfaces, which contained 6.25 mg of compound A (free form) per tablet, a film-coated tablet with a score line on both surfaces, which contained 12.5 mg of compound A (free form) per tablet and a film-coated tablet with a score line on both surfaces, which contained 25 mg of compound A (free form) per tablet. A tableting trouble was not observed in this Example.

TABLE 15

|  |  | dose | | | |
| --- | --- | --- | --- | --- | --- |
|  |  | 3.125 mg | 6.25 mg | 12.5 mg | 25 mg |
|  | plain tablet | | | | |
| component (A) | compound A (benzoate) | 4.25 mg | 8.50 mg | 17.00 mg | 34.00 mg |
|  | mannitol | 109.45 mg | 105.20 mg | 96.70 mg | 79.70 mg |
|  | microcrystalline cellulose | 15.00 mg | 15.00 mg | 15.00 mg | 15.00 mg |
|  | hydroxypropyl- cellulose | 4.50 mg | 4.50 mg | 4.50 mg | 4.50 mg |
| component (B) | microcrystalline cellulose | 7.50 mg | 7.50 mg | 7.50 mg | 7.50 mg |
|  | croscarmellose sodium | 7.50 mg | 7.50 mg | 7.50 mg | 7.50 mg |
|  | magnesium stearate | 1.80 mg | 1.80 mg | 1.80 mg | 1.80 mg |
|  | film coating | | | | |
|  | hypromellose 2910 | 5.388 mg | 5.340 mg | 5.388 mg | 5.340 mg |
|  | titanium oxide | 0.60 mg | 0.60 mg | 0.60 mg | 0.60 mg |
|  | yellow ferric oxide | — mg | — mg | 0.012 mg | 0.06 mg |
|  | red ferric oxide | 0.012 mg | 0.06 mg | — mg | — mg |
|  | macrogol 6000 | 0.1 mg | 0.1 mg | 0.1 mg | 0.1 mg |
|  | total | 156.10 mg | 156.10 mg | 156.10 mg | 156.10 mg |

TABLE 16

|  |  | dose | | | |
| --- | --- | --- | --- | --- | --- |
|  |  | 3.125 mg | 6.25 mg | 12.5 mg | 25 mg |
|  | plain tablet | | | | |
| component (A) | hydroxypropyl- cellulose | 2025 g | 2025 g | 2025 g | 2025 g |
|  | purified water | 31725 g | 31725 g | 31725 g | 31725 g |
|  | compound A (benzoate) | 1913 g | 3825 g | 7650 g | 15300 g |
|  | mannitol | 49253 g | 47340 g | 43515 g | 35865 g |
|  | microcrystalline cellulose | 6750 g | 6750 g | 6750 g | 6750 g |
| component (B) | microcrystalline cellulose | 3375 g | 3375 g | 3375 g | 3375 g |
|  | croscarmellose sodium | 3375 g | 3375 g | 3375 g | 3375 g |
|  | magnesium stearate | 810.0 g | 810.0 g | 810.0 g | 810.0 g |
|  | film coating | | | | |
|  | hypromellose 2910 | 4043 g | 4007 g | 4043 g | 4007 g |
|  | titanium oxide | 450.2 g | 450.2 g | 450.2 g | 450.2 g |
|  | yellow ferric oxide | — g | — g | 9.004 g | 45.02 g |
|  | red ferric oxide | 9.004 g | 45.02 g | — g | — g |
|  | purified water | 40523 g | 40523 g | 40523 g | 40523 g |
|  | macrogol 6000 | 1842 g | 1842 g | 1842 g | 1842 g |
|  | purified water | 16580 g | 16580 g | 16580 g | 16580 g |

Example 13

Benzoate of compound A, mannitol and microcrystalline cellulose according to the formulation of Table 17 were uniformly mixed in a fluidized bed granulation dryer (FD-WSG-60, POWREX CORPORATION), and the mixture was granulated by spraying an aqueous solution of hydroxypropylcellulose and dried therein. The obtained granules were pulverized by a powermill grinder (P-7S, Showa Chemical Machinery) using a 1.5 mmφ punching screen. To the obtained sized powder were added microcrystalline cellulose, magnesium stearate and croscarmellose sodium or carmellose calcium or low-substituted hydroxypropylcellulose according to the formulation shown in Table 17, and they were mixed in a tumbler mixer (TM-15, Showa Chemical Machinery) to give granules for tableting. The granules were punched by a rotary tableting machine (Correct 12HUK, Kikusui Seisakusho, Ltd.) with a 9.0 mm×5.0 mm oval punch to give a plain tablet weighting 150 mg, which contained 25 mg of compound A (free form) per tablet. A tableting trouble was not observed in this Example.

TABLE 17

| | | dose | | |
|---|---|---|---|---|
| | | 25 mg | 25 mg | 25 mg |
| | | plain tablet | | |
| component (A) | compound A (benzoate) | 34.0 mg | 34.0 mg | 34.0 mg |
| | mannitol | 79.7 mg | 79.7 mg | 79.7 mg |
| | microcrystalline cellulose | 15.0 mg | 15.0 mg | 15.0 mg |
| | hydroxypropyl-cellulose | 4.5 mg | 4.5 mg | 4.5 mg |
| component (B) | microcrystalline cellulose | 7.5 mg | 7.5 mg | 7.5 mg |
| | croscarmellose sodium | 7.5 mg | — mg | — mg |
| | carmellose calcium | — mg | 7.5 mg | — mg |
| | low-substituted hydroxypropyl-cellulose | — mg | — mg | 7.5 mg |
| | magnesium stearate | 1.8 mg | 1.8 mg | 1.8 mg |
| | total | 150.0 mg | 150.0 mg | 150.0 mg |

Experimental Example 1

The average tablet hardness of the plain tablets (all 12.5 mg tablets) obtained in Comparative Example 1 and Example 3 was measured at a tableting pressure of 10 kN. The results are shown in Table A.

TABLE A

| | hardness (N) |
|---|---|
| Comparative Example 1 | 61.15 |
| Example 3 | 129.09 |

According to the above results, the tablet of the present invention could be produced without a tableting trouble, and was shown to not decrease the tablet hardness.

Experimental Example 2

According to the Japanese Pharmacopoeia Paddle Method (50 rpm, 37° C., 0.01N HCl 900 mL, n=6), the dissolution behavior of compound A from the plain tablet (12.5 mg tablet; tableting pressure 10 kN) obtained in Example 3 was measured. The results of the drug dissolution rate in 15 min after the dissolution test are shown in Table B.

TABLE B

| | average dissolution rate ± S.D. (%) |
|---|---|
| Example 3 | 106.13 ± 0.29 |

From the results shown above, the tablet of the present invention could be produced without a tableting trouble, and was shown to not cause delayed dissolution of a pharmaceutically active ingredient.

INDUSTRIAL APPLICABILITY

The present invention is useful for tableting a pharmaceutically active ingredient easily inducing a tableting trouble, and has advantages in that a tablet superior in the tablet formability, dissolution property of pharmaceutically active ingredient, and the like can be provided without causing a tableting trouble.

While some of the embodiments of the present invention have been described in detail in the above, it is possible, however, for those of ordinary skill in the art to make various modifications and changes to the particular embodiments shown without substantially departing from the novel teaching and advantages of the present invention. Such modifications and changes are encompassed in the spirit and scope of the present invention as set forth in the appended claims.

This application is based on application No. 2007-023584 filed in Japan, the contents of which are incorporated hereinto by reference.

The invention claimed is:

1. A tablet comprising the following (A) and (B):
   (A) a granule comprising 2-[[6-[(3R)-3-amino-1-piperidinyl]-3,4-dihydro-3-methyl-2,4-dioxo-1(2H)-pyrimidinyl]methyl]-benzonitrile or a salt thereof as a sole pharmaceutically active ingredient in the tablet and microcrystalline cellulose;
   (B) a tableting aid comprising magnesium stearate and microcrystalline cellulose,
   wherein the granule of (A) further comprises mannitol.

2. The tablet of claim 1, wherein the content of the microcrystalline cellulose of (A) and the microcrystalline cellulose of (B) in the tablet is 5-40 wt % and 2-20 wt %, respectively.

3. The tablet of claim 1, wherein the hardness is 70-200 N.

4. The tablet of claim 1, wherein not less than 85% of the pharmaceutically active ingredient is dissolved out in 15 min when the tablet is subjected to a dissolution test according to the Paddle Method at 37° C., 50 rpm using 0.01N hydrochloric acid or the Japanese Pharmacopoeia 2nd fluid (pH 6.8) as a test solution.

5. The tablet of claim 1, wherein the tablet further comprises a binding aid consisting of hydroxypropylcellulose.

6. The tablet of claim 1, wherein the tablet does not contain polyvinylpyrrolidone.

7. A method of producing a tablet, which comprises mixing (A) a granule comprising 2-[[6-[(3R)-3-amino-1-piperidinyl]-3,4-dihydro-3-methyl-2,4-dioxo-1(2H)-pyrimidinyl]methyl]-benzonitrile or a salt thereof as a sole pharmaceutically active ingredient in the tablet and microcrystalline cellulose, and (B) a tableting aid comprising magnesium stearate and microcrystalline cellulose, and then punching the mixture,
   wherein the granule of (A) further comprises mannitol.

8. The method of claim 7, wherein the content of the microcrystalline cellulose of (A) and the microcrystalline cellulose of (B) in the tablet is 5-40 wt % and 2-20 wt %, respectively.

9. A tablet obtained by the method of claim 7.

* * * * *